US008003099B2

(12) United States Patent
Auer et al.

(10) Patent No.: US 8,003,099 B2
(45) Date of Patent: Aug. 23, 2011

(54) ANTIBODIES AGAINST HUMAN IL17 AND USES THEREOF

(75) Inventors: Johannes Auer, Schwaigen (DE); Nikolaos Dimoudis, Wielenbach (DE); Guy Georges, Habach (DE); Petra Hanke, Munich (DE); Hendrik Knoetgen, Penzberg (DE); Ekkehard Moessner, Kreuzlingen (CH); Claire Louise Langrish, Palo Alto, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 12/586,893

(22) Filed: Sep. 29, 2009

(65) Prior Publication Data

US 2010/0080812 A1    Apr. 1, 2010

(30) Foreign Application Priority Data

Sep. 29, 2008 (EP) ..................... 08017155

(51) Int. Cl.
*A61K 39/00* (2006.01)
*A61K 39/395* (2006.01)
(52) U.S. Cl. ............. 424/133.1; 530/388.23; 530/387.3; 530/351; 530/809; 435/69.1
(58) Field of Classification Search ........................ None
See application file for complete search history.

(56) References Cited

U.S. PATENT DOCUMENTS 6,063,372 A    5/2000 Banchereau et al.
6,274,711 B1   8/2001 Goldstein et al.

FOREIGN PATENT DOCUMENTS

| WO | 9518826 A2 | 7/1995 |
|---|---|---|
| WO | 9617939 A1 | 6/1996 |
| WO | 9715320 A1 | 5/1997 |
| WO | 9935276 A1 | 7/1999 |
| WO | 0069436 A1 | 11/2000 |
| WO | 2005051422 A1 | 6/2005 |
| WO | 2006013107 A1 | 2/2006 |
| WO | 2008002115 A1 | 1/2008 |

OTHER PUBLICATIONS

Hellings, P. W., et. al. "Interleukin-17 Orchestrates the Granulocyte Influx into Airways after Allergen Inhalation in a Mouse Model of Allergic Asthma," American Journal of Respir. Cell. Molecular Biology, 2003, vol. 28, pp. 42-50.
Komiyama, Y., et. al. "IL-17 Plays an Important Role in the Development of Experimental Autoimmune Encephalomyelitis1," The Journal of Immunology, 2006, vol. 177, pp. 566-573.
Kotake, S., et. al. "IL-17 in synovial fluids from patients with rheumatoid arthritis is a potent stimulator of osteoclastogenesis," The Journal of Clinical Investigation, 1999, vol. 103 (9), pp. 1345-1352.
Ziolkowska, M., et. al. "High Levels of IL-17 in Rheumatoid Arthritis Patients: IL-15 Triggers In Vitro IL-17 Production Via Cyclosporin A-Sensitive Mechanism1," The American Association of Immunologists, 2000, vol. 164, pp. 2832-2838.

*Primary Examiner* — Dong Jiang
(74) *Attorney, Agent, or Firm* — Robert C. Hall

(57) ABSTRACT

An antibody binding to IL-17 characterized by binding to the same IL-17 epitope to which monoclonal antibody 3C1 binds, and being of human IgG1 isotype modified in the hinge region at amino acid position 216-240, preferably at amino acid position 220-240, between $C_H1$ and $C_H2$ and/or in the second inter-domain region at amino acid position 327-331 between $C_H2$ and $C_H3$ has advantageous properties for the treatment of inflammatory diseases.

17 Claims, No Drawings ary composition. Preferably the pharmaceutical composition comprises
ANTIBODIES AGAINST HUMAN IL17 AND USES THEREOF The present invention relates to antibodies against human IL17A (IL17 antibody), methods for their production, pharmaceutical compositions containing said antibodies, and uses thereof.

BACKGROUND OF THE INVENTION

Human IL-17A (CTLA-8, Swiss Prot Q16552, further named as IL-17) is a pro-inflammatory cytokine produced by a subset of memory T cells (called Th17) that has been implicated in the pathogenesis of MS. IL-17A plays a role in the induction of other inflammatory cytokines, chemokines and adhesion molecules. Treatment of animals with IL-17A neutralizing antibodies decreases disease incidence and severity in autoimmune encephalomyelitis (Komiyama, Y. et al., *J. Immunol.* 177 (2006) 566-573). IL-17A is over-expressed in the cerebrospinal fluid of MS patients (Hellings, P. W. et al., *Am. J. Resp. Cell Mol. Biol.* 28 (2003) 42-50; Matusevicius, D. et al., *Multiple Sclerosis* 5 (1999) 101-104; WO 2005/051422). In addition, IL-17A neutralizing antibodies reduce severity and incidence of mouse RA model of collagen induced arthritis, and high levels of IL-17A can be detected in the synovial fluid of inflamed joints from RA patients (Ziolkovvska, M. et al., *J. Immunol.* 164 (2000) 2832-38; Kotake, S. et al., *J. Clin. Invest.* 103 (1999) 1345-52; Hellings, P. W. et al., *Am. J. Resp. Cell Mol. Biol.* 28 (2003) 42-50).

WO 96/17939, U.S. Pat. No. 5,716,623; WO 95/18826; WO 97/15320; WO 99/35276 and WO 00/69436 WO 95/18826 U.S. Pat. Nos. 6,274,711, 6,274,711, WO 97/15320, U.S. Pat. No. 6,063,372, WO 2006/013107 and WO200802115 relate to IL-17A and antibodies against IL-17A.

SUMMARY OF THE INVENTION

The invention comprises an antibody binding to IL-17, characterized in that the heavy chain variable domain comprises a CDR3 region of SEQ ID NO: 1, a CDR2 region of SEQ ID NO:2 or 9 and a CDR1 region of SEQ ID NO:3 and in that the light chain variable domain comprises a CDR3 region of SEQ ID NO: 4, a CDR2 region of SEQ ID NO:5 and a CDR1 region of SEQ ID NO:6. Preferably the antibody is characterized in that the heavy chain variable domain comprises SEQ ID NO:7 or 10. Preferably the antibody is characterized in that the heavy chain variable domain comprises SEQ ID NO:7 or 10 and the light chain variable domain comprises SEQ ID NO:8. Preferably the antibody binding to IL-17 and being characterized by the above mentioned amino acid sequences and amino acid sequence fragments is of human IgG1 isotype modified in the hinge region at amino acid position 216-240, preferably at amino acid position 220-240, between $C_H1$ and $C_H2$ and/or in the second inter-domain region at amino acid position 327-331 between $C_H2$ and $C_H3$. Preferably the antibody comprises mutations L234A (alanine instead of leucine at amino acid position 234) and L235A. A preferred heavy chain constant region including mutations L234A and L235A is shown in SEQ ID NO:11.

A preferred hybridoma cell line according to the invention, <hIL-17>1A1.3C1 (antibody 3C1) was deposited with Deutsche Sammlung von Mikroorganismen und Zellkulturen GmbH (DSMZ), Braunschweig, Germany.

| Cell line | Deposit No. | Date of deposit |
|---|---|---|
| <hIL-17>1A1.3C1 | DSM ACC2941 | Aug. 12, 2008 |

An antibody obtainable from said cell lines (antibody 3C1) is a preferred embodiment of the invention. A further embodiment of the invention is a chimeric, humanized or T cell epitope depleted antibody variant of antibody 3C1 (DSM ACC2941). The antibody binds specifically to IL17 with an $IC_{50}$ value of 1 nM or lower. Preferred humanized versions of 3C1 are Mab 106 and Mab 107.

The invention relates further to an antibody binding to IL-17 and being characterized by binding to the same IL-17 epitope to which monoclonal antibody 3C1 binds. The antibody binds to IL-17 with an affinity of at least $10^{-8}$ $M^{-1}$ to $10^{-12}$ $M^{-1}$, is of human IgG1 isotype modified in the hinge region at amino acid position 216-240, preferably at amino acid position 220-240, between $C_H1$ and $C_H2$ and/or in the second inter-domain region at amino acid position 327-331 between $C_H2$ and $C_H3$. Preferably the antibody is of human IgG1 isotype comprising mutations L234A (alanine instead of leucine at amino acid position 234) and L235A.

Preferably the antibody is a humanized or human antibody. Preferably the antibody according to the invention inhibits at a concentration of 100 ng/ml cynomolgus IL-17A induced IL-6 and IL-8 production in a cytokine release assay with an $IC_{50}$ value of 1.5 nM or lower, using cynomolgus dermal fibroblasts.

A further embodiment of the invention is a pharmaceutical composition comprising an antibody according to the invention. Preferably the pharmaceutical composition comprises an antibody characterized by binding to the same IL-17 epitope to which monoclonal antibody 3C1 binds. Preferably the antibody of the pharmaceutical composition binds to IL-17 with an affinity of at least $10^{-8}$ $M^{-1}$ to $10^{-12}$ $M^{-1}$ is of human IgG1 isotype modified in the hinge region at amino acid position 216-240, preferably at amino acid position 220-240, between $C_H1$ and $C_H2$ and/or in the second inter-domain region at amino acid position 327-331 between $C_H2$ and $C_H3$. Preferably the antibody is of human IgG1 isotype comprising mutations L234A (alanine instead of leucine at amino acid position 234) and L235A.

A further embodiment of the invention is the use of an antibody according to the invention for the manufacture of a pharmaceutical composition. Preferably the pharmaceutical composition comprises an antibody characterized by binding to the same IL-17 epitope to which monoclonal antibody 3C1 binds. Preferably the antibody of the pharmaceutical composition binds to IL-17 with an affinity of at least $10^{-8}$ $M^{-1}$ to $10^{-12}$ $M^{-1}$, is of human IgG1 isotype modified in the hinge region at amino acid position 216-240, preferably at amino acid position 220-240, between $C_H1$ and $C_H2$ and/or in the second inter-domain region at amino acid position 327-331 between $C_H2$ and $C_H3$. Preferably the antibody is of human IgG1 isotype comprising mutations L234A (alanine instead of leucine at amino acid position 234) and L235A.

A further embodiment of the invention is the use of an antibody according to the invention for the treatment of multiple sclerosis, rheumatoid arthritis, psoriasis, Crohn's disease, chronic obstructive pulmonary disease (COPD), asthma, and transplant rejection. A further embodiment of the invention is a method for the manufacture of a pharmaceutical composition comprising an antibody according to the invention. Preferably the pharmaceutical composition comprises an antibody characterized by binding to the same IL-17 epitope to which monoclonal antibody 3C1 binds. Preferably the antibody of the pharmaceutical composition binds to IL-17 with an affinity of at least $10^{-8}$ $M^{-1}$ to $10^{-12}$ $M^{-1}$, is of human IgG1 isotype modified in the hinge region at amino acid position 216-240, preferably at amino acid position 220-240, between $C_H1$ and $C_H2$ and/or in the second inter-domain region at amino acid position 327-331 between $C_H2$ and $C_H3$. Preferably the antibody is of human IgG1 isotype comprising mutations L234A (alanine instead of leucine at amino acid position 234) and L235A.

A further embodiment of the invention is a nucleic acid encoding a heavy chain of an antibody binding to IL-17, characterized in comprising a heavy chain CDR3 region of SEQ ID NO:1 and preferably mutations L234A and L235A in the IgG1 heavy chain constant domain. Preferably the antibody comprises in addition a heavy chain CDR2 region of SEQ ID NO:2 or 9 and a CDR1 region of SEQ ID NO:3. A further embodiment of the invention is a nucleic acid encoding a light chain of an antibody binding to IL-17, characterized by comprising a light chain CDR3 region according to the invention and preferably mutations L234A and L235A in the IgG1 heavy chain constant domain. Preferably the antibody comprises in addition a heavy chain CDR2 region of SEQ ID NO:2 or 9 and a CDR1 region of SEQ ID NO:3. A further embodiment of the invention is a nucleic acid encoding an antibody according to the invention characterized by comprising a heavy chain variable domain of SEQ ID NO: 7 or 10 and a variable light chain domain of SEQ ID NO:8 and preferably mutations L234A and L235A in the heavy chain IgG1 constant domain.

The antibody according to the invention is characterized in that the constant chains are of human origin. Such constant chains are well known in the state of the art and e.g. described by Kabat (see e.g. Johnson, G. and Wu, T. T., *Nuc Acids Res.* 28 (2000) 214-18). For example, a useful human heavy chain constant region comprises an amino acid sequence of SEQ ID NO:11 with mutations L234A and L235A. For example, a useful human light chain constant region comprises an amino acid sequence of a kappa-light chain constant region of SEQ ID NO:12. It is further preferred that the antibody is of mouse origin and comprises the antibody variable sequence frame of a mouse antibody according to Kabat (see e.g., Johnson, G. and Wu, T. T., supra).

The antibody according to the invention is especially characterized by inhibiting the release of Interleukin-8 (IL-8) from CCD25-SK cells. The antibody according to the invention specifically neutralizes IL17-mediated cell activation with an $IC_{50}$ value of 0.5 nM (16 ng/ml) or lower. The antibody according to the invention specifically binds to IL17 with an $IC_{50}$ value of 1 nM or lower.

The antibody according to the invention is preferably of human isotype IgG1. Preferred γ1 heavy chain constant regions are shown in SEQ ID NO:11 and in SEQ ID NO:11 without L234A and L235A mutations.

The antibody according to the invention is preferably characterized by not binding human complement factor C1q and avoid therefore CDC effector function.

The antibody according to the invention is preferably of human IgG1 isotype modified in the hinge region at amino acid position 216-240, preferably at amino acid position 220-240, between $C_H1$ and $C_H2$ and/or in the second inter-domain region at amino acid position 327-331 between $C_H2$ and $C_H3$. The antibody according to the invention is preferably characterized by being of human IgG1 isotype, containing at least one mutation in, L234 (leucine at amino acid position 234), L235, D270, N297, E318, K320, K322, P331, and/or P329 (numbering according to EU index). Preferably the antibody is of human IgG1 isotype comprising mutations L234A (alanine instead of leucine at amino acid position 234) and L235A.

The invention further provides expression vectors containing nucleic acid according to the invention capable of expressing said nucleic acid in a prokaryotic or eukaryotic host cell, and host cells containing such vectors for the recombinant production of such an antibody. The invention further comprises a prokaryotic or eukaryotic host cell comprising a vector according to the invention. The invention further comprises a method for the production of a recombinant human or humanized antibody according to the invention, characterized by expressing a nucleic acid according to the invention in a prokaryotic or eukaryotic host cell and recovering said antibody from said cell or the cell culture supernatant. The invention further comprises the antibody obtainable by such a recombinant method.

Antibodies according to the invention show benefits for patients in need of an IL-17 targeting therapy. The antibodies according to the invention have new and inventive properties causing a benefit for a patient suffering from such an immunological disease, especially suffering from multiple sclerosis, rheumatoid arthritis, psoriasis, Crohn's disease, chronic obstructive pulmonary disease (COPD), asthma, or transplant rejection. The antibodies according to the invention are not causing susceptability for staphylococcal and enteric bacterial infections of the treated patient. The invention further provides a method for treating a patient suffering from multiple sclerosis, rheumatoid arthritis, psoriasis, Crohn's disease, chronic obstructive pulmonary disease (COPD), asthma, or transplant rejection comprising administering to a patient diagnosed as having such a disease (and therefore being in need of such a therapy) an effective amount of an antibody binding to IL-17 according to the invention. The antibody is administered preferably in a pharmaceutical composition. A further embodiment of the invention is a method for the treatment of a patient suffering from multiple sclerosis, rheumatoid arthritis, psoriasis, Crohn's disease, chronic obstructive pulmonary disease (COPD), asthma, or transplant rejection, characterized by administering to the patient an antibody according to the invention. The invention further comprises the use of an antibody according to the invention for the treatment of a patient suffering from multiple sclerosis, rheumatoid arthritis, psoriasis, Crohn's disease, chronic obstructive pulmonary disease (COPD), asthma, or transplant rejection and for the manufacture of a pharmaceutical composition according to the invention. In addition, the invention comprises a method for the manufacture of a pharmaceutical composition according to the invention.

The invention further comprises a pharmaceutical composition comprising an antibody according to the invention, optionally together with a buffer and/or an adjuvant useful for the formulation of antibodies for pharmaceutical purposes. The invention further provides pharmaceutical compositions comprising an antibody according to the invention in a pharmaceutically acceptable carrier. In one embodiment, the pharmaceutical composition may be included in an article of manufacture or kit.

DETAILED DESCRIPTION OF THE INVENTION

The term "antibody" encompasses the various forms of antibody structures including but not being limited to whole antibodies and antibody fragments. The antibody according to the invention is preferably a humanized antibody, chimeric antibody, or further genetically engineered antibody as long as the characteristic properties according to the invention are retained. "Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Huston, J. S., *Meth Enzymol.* (1991) 203:46-52. In addition, antibody fragments comprise single chain polypeptides having the characteristics of a $V_H$ domain, namely being able to assemble together with a $V_L$ domain, or of a $V_L$ domain binding to IL-17, namely being able to assemble together with a $V_H$ domain to a functional antigen binding site and thereby providing the properties of an antibody according to the invention. The terms "monoclonal antibody" or "monoclonal antibody composition" as used herein refer to a preparation of antibody molecules of a single amino acid composition. The term "humanized antibody" refers to antibodies in which the framework and/or "complementary determining regions" (CDR) have been modified to comprise the CDR of an immunoglobulin of different species as compared to that of the parent immunoglobulin. In a preferred embodiment, a mouse CDR is grafted into the framework region of a human antibody to prepare the "humanized antibody". See, e.g., Riechmann, L., et al., *Nature* 332 (1988) 323-27; and Neuberger, M. S., et al., *Nature* 314 (1985) 268-70.

The term "binding to IL-17" as used herein means binding of the antibody to human IL-17 in an ELISA binding assay. Binding is found if the antibody causes an S/N (signal/noise) ratio of 7:1 or more at an antibody concentration of 1 µg/ml. The antibody according to the invention specifically binds to human IL-17A and with an $IC_{50}$ value of 1 nM (0.15 µg/ml) or lower. The antibody does not bind to IL-17 B, C, D, E, and F (S/N (signal/noise) ratio of lower than 7:1) and is therefore specifically binding to IL-17A. Binding to IL-17 A and variants is performed by ELISA using immobilized IL-17 or variant.

The term "epitope" denotes a protein determinant capable of specifically binding to an antibody. Epitopes usually consist of chemically active surface groupings of molecules such as amino acids or sugar side chains and usually epitopes have specific three dimensional structural characteristics, as well as specific charge characteristics. Conformational and non-conformational epitopes are distinguished in that the binding to the former but not the latter is lost in the presence of denaturing solvents. Preferably an antibody according to the invention binds specifically to native but not to denatured IL-17. The IL-17 antibody of the invention binds to the same epitope on IL-17 to which antibody Mab317 binds. The epitope binding property of an IL-17 antibody of the present invention may be determined using techniques known in the art. The IL-17 antibody is tested by an in vitro crossblocking binding assay to determine the ability of the test antibody to hinder the binding of antibody Mab317 to IL-17. If there is a displacement of the test antibody by antibody Mab317 for at least 15%, then the epitopes are in near proximity.

The "variable domain" (variable domain of a light chain ($V_L$), variable domain of a heavy chain ($V_H$)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refers to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The terms "nucleic acid" or "nucleic acid molecule", as used herein, are intended to include DNA molecules and RNA molecules. A nucleic acid molecule may be single-stranded or double-stranded, but preferably is double-stranded DNA. A nucleic acid is "operably linked" when it is placed into a functional relationship with another nucleic acid. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operable linked" means that the DNA sequences being linked are colinear, and, in the case of a secretory leader, contiguous and in reading frame. However, enhancers do not have to be contiguous. Linking is accomplished by ligation at convenient restriction sites. If such sites do not exist, synthetic oligonucleotide adaptors or linkers are used in accordance with conventional practice. As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

The "Fc part" of an antibody is not involved directly in binding of an antibody to an antigen, but exhibits various effector functions. An "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called α, δ, ε, γ, and μ, respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described by, e.g., Boakle, R. J. et al., Nature 282 (1979) 742-43; Lukas, T. J. et al., J. Immunol. 127 (1981) 2555-60; Brunhouse, R. and Cebra, J. J., Mol. Immunol. 16 (1979) 907-17; Burton, D. R. et al., Nature 288 (1980) 338-44; Thommesen, J. E. et al., Mol. Immunol. 37 (2000) 995-1004; Idusogie, E. E. et al., J. Immunol. 164 (2000) 4178-84; Hezareh, M. et al., J. Virology 75 (2001) 12161-68; Morgan, A. et al., Immunology 86 (1995) 319-24; EP 0307434. Such binding sites are, e.g., L234, L235, D270, N297, E318, K320, K322, P331, and P329 (numbering according to EU index of Kabat, see below). Antibodies of subclass IgG1, IgG2 and IgG3 usually show complement activation and C1q binding, whereas IgG4 does not activate the complement system and does not bind C1q.

The antibody according to the invention comprises an Fc part from human origin which is Fc part of a human antibody of the subclass IgG1. For the Fc part of an antibody according to the invention preferably no C1q binding as defined below can be detected.

The invention therefore comprises an antibody according to the invention, characterized in that said antibody binds IL-17, contains an Fc part from human origin, and does not bind human complement factor C1q and therefore avoids CDC effector function Preferably an antibody according to the invention is in regard to Fcγ receptor binding of human IgG1 or IgG2 subclass, with a mutation in L234, L235, and/or D265, and/or contains the PVA236 mutation. Preferred are the mutations L234A, L235A, L235E, and/or PVA236 (PVA236 means that the amino acid sequence ELLG (given in one letter amino acid code) from amino acid position 233 to 236 of IgG1 or EFLG of IgG4 is replaced by PVA). The present invention thus provides an antibody according to the invention being characterized in that said antibody is an antibody of human subclass IgG1, containing at least one mutation in L234, L235, D270, N297, E318, K320, K322, P331 and/or P329. In one embodiment the antibody is a human antibody. In another embodiment the antibody is a humanized antibody. In one embodiment the present invention provides an antibody according to the invention, containing an Fc part derived from human origin, and being characterized in that said antibody is an antibody of human subclass IgG1, containing at least one mutation in L234, L235, D270, N297, E318, K320, K322, P331 and wherein the antibody binds to IL-17 with a $K_D$ value of less than $10^{-8}$ M in a BIAcore assay. In another embodiment the $K_D$ range is $10^{-11}$ to $10^{-9}$ M.

C1q binding can be measured according to Idusogie, E. E., et al., J. Immunol. 164 (2000) 4178-84. No C1q binding according to the invention is characterized in that if in such an assay wherein an ELISA plate is coated with different concentrations of the antibody, human C1q is added. C1q binding is detected by an antibody directed against human C1q followed by peroxidase-labeled conjugate detection with peroxidase substrate ABTS® (2,2'-azino-di-[3-ethylbenzthiazolinesulfonate]). No C1q binding according to the invention is found if the optical density (OD) at 405 nm is for the test antibody lower than 0.05 at an antibody concentration of 10 μg/ml.

The antibody according to the invention is preferably characterized in that the constant chains are of human origin. Such constant chains are well known in the state of the art and described, e.g., by Kabat (see e.g. Johnson, G., and Wu, T. T., Nuc Acids Res. 28 (2000) 214-18). For example, a useful human heavy chain constant region comprises SEQ ID NO:23. For example, a useful human light chain constant region comprises an amino acid sequence of a kappa-light chain constant region of SEQ ID NO: 12.

A further embodiment of the invention is a nucleic acid encoding a heavy and a light chain of an antibody according to the invention.

The invention comprises a method for the treatment of a patient in need of therapy, characterized by administering to the patient a therapeutically effective amount of an antibody according to the invention. The invention comprises the use of an antibody according to the invention for therapy. The invention comprises the use of an antibody according to the invention for the preparation of a medicament for the prophylaxis and treatment of inflammatory and thrombotic disorders. The invention comprises the use of an antibody according to the invention for the treatment of inflammatory diseases, preferably for the treatment of Chronic obstructive pulmonary disorder (COPD), multiple sclerosis, and rheumatoid arthritis.

The antibodies according to the invention include, in addition, such antibodies having "conservative sequence modifications" (variant antibodies), nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, a predicted nonessential amino acid residue in a human anti-IL-17 antibody can be preferably replaced with another amino acid residue from the same side chain family. A "variant" anti-IL-17 antibody, refers therefore herein to a molecule which differs in amino acid sequence from a "parent" anti-IL-17 antibody amino acid sequence by up to ten, preferably from about two to about five, additions, deletions and/or substitutions in one or more variable region of the parent antibody. Amino acid substitutions can be performed by mutagenesis based upon molecular modeling as described by Riechmann, L., et al., Nature 332 (1988) 323-27 and Queen, C., et al., Proc. Natl. Acad. Sci. USA 86 (1989) 10029-33.

A further embodiment of the invention is a method for the production of an antibody against IL-17 which does not bind Fcγ receptor and/or C1q, characterized in that the sequence of a nucleic acid encoding the heavy chain of a human IgG1 type antibody binding to IL-17 is modified in such a manner that said modified antibody does not bind C1q and/or Fcγ receptor, said modified nucleic acid and the nucleic acid encoding the light chain of said antibody are inserted into an expression vector, said vector is inserted in a eukaryotic host cell, the encoded protein is expressed and recovered from the host cell or the supernatant.

Identity or homology with respect to the sequence is defined herein as the percentage of amino acid residues in the candidate sequence that are identical with the parent sequence, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind human IL-17 and preferably has properties, which are superior to those of the parent antibody. For example, the variant may have reduced side effects during treatment.

The "parent" antibody comprises the CDR regions of antibody 3C1 and is preferably used for the preparation of the variant. Preferably, the parent antibody has a human framework region and, if present, has a human antibody constant region or human antibody constant domains. For example, the parent antibody may be a humanized or a human antibody.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or *E. coli* cells, and the antibody is recovered from the cells (from the supernatant or after cells lysis). Recombinant production of antibodies is well-known in the state of the art and described, for example, in the review articles of Makrides, S. C., *Protein Expr. Purif.* 17 (1999) 183-202; Geisse, S., et al., *Protein Expr. Purif.* 8 (1996) 271-82; Kaufman, R. J., *Mol. Biotechnol.* 16 (2000) 151-60; Werner, R. G., *Drug Res.* 48 (1998) 870-80. The antibodies may be present in whole cells, in a cell lysate, or in a partially purified, or substantially pure form. Purification is performed in order to eliminate other cellular components or other contaminants, e.g., other cellular nucleic acids or proteins, by standard techniques, including column chromatography and others well known in the art. See Ausubel, F., et al., ed. Current Protocols in Molecular Biology, Greene Publishing and Wiley Interscience, New York (1987). Expression in NS0 cells is described by, e.g., Barnes, L. M., et al., *Cytotechnology* 32 (2000) 109-23; Barnes, L. M., et al., *Biotech. Bioeng.* 73 (2001) 261-70. Transient expression is described by, e.g., Durocher, Y., et al., *Nucl. Acids. Res.* 30 (2002) E9. Cloning of variable domains is described by Orlandi, R., et al., *Proc. Natl. Acad. Sci. USA* 86 (1989) 3833-37; Carter, P., et al., *Proc. Natl. Acad. Sci. USA* 89 (1992) 4285-89; Norderhaug, L., et al., *J. Immunol. Meth.* 204 (1997) 77-87. A preferred transient expression system (HEK 293) is described by Schlaeger, E.-J. and Christensen, K., in *Cytotechnology* 30 (1999) 71-83, and by Schlaeger, E.-J., in *J. Immunol. Meth.* 194 (1996) 191-99. Monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells, such as HEK 293 cells, CHO cells, or myeloma cells that do not otherwise produce immunoglobulin protein, to obtain the synthesis of recombinant monoclonal antibodies in the host cells.

Amino acid sequence variants of human IL-17 antibody are prepared by introducing appropriate nucleotide changes into the antibody encoding DNA, or by peptide synthesis. Such modifications can be performed, however, only in a very limited range, e.g. as described above. For example, the modifications do not alter the abovementioned antibody characteristics such as the IgG isotype and epitope binding, but may improve the yield of the recombinant production, protein stability, or facilitate the purification. Any cysteine residue not involved in maintaining the proper conformation of the anti-IL-17 antibody may also be substituted, generally with serine, to improve the oxidative stability of the molecule and to prevent aberrant crosslinking. Conversely, cysteine bond(s) may be added to the antibody to improve its stability (particularly where the antibody is an antibody fragment such as an Fv fragment). Another type of amino acid variant of the antibody alters the original glycosylation pattern of the antibody. By "altering" is meant removing one or more carbohydrate moieties found in the antibody and/or adding one or more glycosylation sites that are not present in the antibody. Glycosylation of antibodies is typically N-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Nucleic acid molecules encoding amino acid sequence variants of anti-IL-17 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-IL-17 antibody.

Another type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; 4,179,337.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

In another aspect, the present invention provides a composition, e.g., a pharmaceutical composition, containing one or a combination of monoclonal antibodies, or the antigen-binding portion thereof, of the present invention, formulated together with a pharmaceutically acceptable carrier. As used herein, "pharmaceutically acceptable carrier" includes any and all solvents, dispersion media, coatings, antibacterial and antifungal agents, isotonic and absorption/resorption delaying agents, and the like that are physiologically compatible. Preferably, the carrier is suitable for injection or infusion. A composition of the present invention can be administered by a variety of methods known in the art. As will be appreciated by the skilled artisan, the route and/or mode of administration will vary depending upon the desired results. Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution. Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The invention comprises the use of the antibodies according to the invention for the treatment of a patient suffering from multiple sclerosis, rheumatoid arthritis (RA), psoriasis, Crohn's disease, chronic obstructive pulmonary disease (COPD), asthma, and transplant rejection.

A further embodiment of the invention is the use of an anti-IL-17 antibody, preferably an antibody according to the invention, for the treatment of a patient suffering from rheumatoid arthritis, said patient do respond moderate or do not respond to the treatment with a TNF antagonist, anti-CD20 antibody, CTLA4Ig or anti-IL6 antibody. A further embodiment of the invention is the use of an anti-IL-17 antibody, preferably an antibody according to the invention, for the manufacture of a medicament for the treatment of a patient suffering from rheumatoid arthritis, said patient responding moderately or not responding to the treatment with a TNF antagonist, anti-CD20 antibody, CTLA4Ig or anti-IL 6 antibody. TNF antagonists for RA treatment are, for example, infliximab (IFX, Remicade®), etanercept (ETA, Enbrel®), and adalimumab (ADA, Humira®). Anti-IL-17 antibody is preferably administered to the patient who responds moderately or does not respond to a treatment with a TNF antagonist, anti-CD20 antibody, CTLA4Ig or anti-IL6 antibody for at least 3 months, preferably for 6 months.

The invention further provides a method for the manufacture of a pharmaceutical composition comprising an effective amount of an antibody according to the invention together with a pharmaceutically acceptable carrier and the use of the antibody according to the invention for such a method. The invention further provides the use of an antibody according to the invention in an effective amount for the manufacture of a pharmaceutical agent, preferably together with a pharmaceutically acceptable carrier, for the treatment of a patient suffering from multiple sclerosis, rheumatoid arthritis, psoriasis, Crohn's disease, chronic obstructive pulmonary disease (COPD), asthma, and transplant rejection. The invention also provides the use of an antibody according to the invention in an effective amount for the manufacture of a pharmaceutical agent, preferably together with a pharmaceutically acceptable carrier, for the treatment of a patient suffering from multiple sclerosis, rheumatoid arthritis, psoriasis, Crohn's disease, chronic obstructive pulmonary disease (COPD), asthma, and transplant rejection.

DESCRIPTION OF THE SEQUENCES

SEQ ID NO: 1 heavy chain CDR3, Mab 106 and Mab 107
SEQ ID NO: 2 heavy chain CDR2, Mab 106
SEQ ID NO: 3 heavy chain CDR1, Mab 106 and Mab 107
SEQ ID NO: 4 light chain CDR3, Mab 106 and Mab 107
SEQ ID NO: 5 light chain CDR2, Mab 106 and Mab 107
SEQ ID NO: 6 light chain CDR1, Mab 106 and Mab 107
SEQ ID NO: 7 heavy chain variable domain, Mab 106
SEQ ID NO: 8 light chain variable domain, Mab 106 and Mab 107
SEQ ID NO: 9 heavy chain CDR2, Mab 107
SEQ ID NO: 10 heavy chain variable domain, Mab 106
SEQ ID NO: 11 γ1 heavy chain constant region
SEQ ID NO: 12 κ light chain constant region

EXAMPLES

Example 1

Description of Immunization

Immunization was performed within 20 weeks using 5 female Balb/c mice using 250 (1×) and 100 µg (3×) recombinant human IL17 from Peprotech (www.peprotech.com; Cat. Nr.: 200-17 in 1% PBS with 1% Albumin) per mouse.

Example 2

Binding to IL-17 Measured by ELISA

NUNC® Maxisorp plates (96-well) are coated with recombinant human IL-17 (Peprotech #200-17, www.peprotech.com) at a concentration of 0.5 µg/ml in PBS (100 ml/well). Plates are incubated at 37° C. on an orbital shaker with agitation for 2 hours. Thereafter coating solution is removed and 100 µl/well PBSTC (phosphate buffered saline, 0.05% Tween® 20, 2% chicken serum) is added. Plates are incubated at room temperature for 1 h. Blocking solution is removed and samples (blank: PBSTC, samples (10 µg/ml in PBS): anti-human IL-17 antibodies 3C1 and Mab 106 according to the invention; Mab 16-7178-85 of eBioscience (www.ebioscience.com); MAB 317 of R&D Systems (www.rndsystems.com), NVP-AIN-497 (WO 2006013107); are added to the plate (100 µl/well). Plates are incubated at room temperature with agitation. Samples are removed, plates are washed three times with 200 µl/well PBST (phosphate buffered saline, 0.05% Tween® 20) and second antibody (Goat anti-mouse IgG, Fc gamma, HRP conjugate;

Chemicon AP127P, www.Millipore.com) for the detection of mouse antibodies or Goat Anti-human IgG, Fc gamma, HRP conjugate (Chemicon AP113P) for the detection of humanized antibodies is added. The second antibody is diluted 1:10000 in PBSTC and plates are incubated for 1 hour at room temperature with agitation. Second antibody is removed, plates are washed three times with 200 µl/well PBST (phosphate buffered saline, 0.05% Tween®20) and 100 µl/well ABTS® (Roche Diagnostics GmbH) is added. Optical density is measured at 405/492 nm in relation to IL-17A binding (set as 100%). Binding to other human IL-17 subtypes (IL-17B, IL-17C, IL-17D, IL-17E and IL-17F) were performed with the same assay format. Results are shown in Table 1.

TABLE 1

| Antibody | Binding (IL-17A binding set as 100) | | | | | |
|---|---|---|---|---|---|---|
| | IL17A | IL17B | IL17C | IL17D | IL17E | IL17F |
| 3C1 | 100 | 0 | 1 | 0 | 0 | 0 |
| 106 | 100 | 0 | 0 | 0 | 1 | 0 |
| Mab 317 | 100 | 0 | 0 | 0 | 0 | 0 |
| 16-7178-85 | 100 | 7 | 97 | 6 | 5 | 5 |
| NVP-AIN-497 | 100 | 2 | 2 | 0 | 3 | 62 |

Example 3

Preparation of an Expression Plasmid for an Immunoglobulin of Class IgG1

Plasmid 6454 (denoted as p6454 in the following) is the expression plasmid for the expression of an anti-IL-17-antibody (genomically organized expression cassette with retained exon-intron organization) in eukaryotic cells. It comprises the following functional elements:
an origin of replication derived from the vector pUC18 (pUC origin),
a β(beta)-lactamase gene conferring ampicillin resistance in E. coli (Amp),
an expression cassette for the expression of the gamma 1-heavy chain comprising the following elements:
the major immediate-early promoter and enhancer from the human cytomegalovirus (hCMV IE1 promoter),
a synthetic 5'UTR including a Kozak sequence,
a murine immunoglobulin heavy chain signal sequence including the signal sequence intron (L1_Intron_L2),
the cDNA for the heavy chain variable region (VH) arranged with a splice donor site at the 3' end,
the mouse immunoglobulin µ-enhancer region,
the human immunoglobulin heavy chain gamma 1-gene (IGHG1) including exons CH1, Hinge, CH2 and CH3, intervening introns and the 3'UTR bearing the polyadenylation signal sequence,
an expression cassette for the expression of the kappa-light chain comprising the following elements:
the major immediate-early promoter and enhancer from the human cytomegalovirus (hCMV IE1 promoter),
a synthetic 5'UTR including a Kozak sequence,
a murine immunoglobulin heavy chain signal sequence including the signal sequence intron (L1_Intron_L2),
the cDNA for the light chain variable region arranged with a splice donor site at the 3' end (VL),
the intronic mouse Ig-kappa enhancer region,
the human immunoglobulin kappa gene (IGK) including the IGKC exon and the IGK 3'UTR bearing the polyadenylation signal sequence,
an expression cassette for the expression of murine dihydrofolate reductase (DHFR) suitable for auxotrophic selection in eukaryotic cells including
a shortened version of the SV40 early promoter and origin,
the coding sequence for murine DHFR,
the SV40 early polyadenylation signal.
P6454 was transfected into CHO-K1 cells and stable cell lines were isolated after selection with Methotrexate (MTX) and were screened for production of human antibody by ELISA for human IgG.

Example 4

Investigation of Activation of the Complement System (C1q Binding ELISA)

To investigate C1q binding of an antibody according to the invention, an ELISA approach is used. C1q is part of the adaptive immune system and, upon binding to immune complexes, triggers the sequential activation of several zymogens. The enzymes in turn, cause the cleavage of C3 molecules, which can result in the onset of inflammatory reactions, opsonization of foreign or aberrant particles and lysis of cell membranes.

A MTP (Nunc) is coated with the antibodies to be tested in PBS-buffer over night at 4° C. at seven concentrations between 10 µg/mL and 0.156 µg/mL, 100 µl/well. Blocking of free binding sites is done with 3% BPLA (Roche) in PBS for 1 h at RT, 200 µl/well. The MTP is incubated with 2 µg/mL C1q (Quiddel) in 3% BPLA in PBS, 100 µg/mL. The MTP is washed 3× at RT with 0.1% Tween®20 in PBS. Binding was detected by adding polyclonal rabbit anti-C1q antibody (DAKO) at 0.25 µg/mL in 3% BPLA, 0.1% Tween®20 in PBS, 100 µl/well for 1 h at RT. The MTP is washed 3 times at RT with 0.1% Tween20 in PBS. The secondary antibody goat anti-rabbit IgG POD (Jackson Immuno Research) is added at 0.1 µg/mL in 3% Tween 20 in PBS for 1 h at RT, 100 µl/well. After washing the MTP 3 times with 0.1% Tween20 in PBS at RT the MTP is incubated with ABTS solution (Roche) and the absorption at a wavelength of 405 nm is measured with a reference wavelength of 490 nm. Background signals are determined in wells which are not coated with antibodies, but treated by the identical detection procedure. No C1q binding is found if the optical density (OD) at 405 nm for the test antibody is lower than 0.05 at an antibody concentration of 10 µg/ml.

Example 5

Epitope Region Mapping Via Biacore Crossblocking Experiments

All measurements were performed using the BIAcore 3000 instrument at 25° C. The system and sample buffer was HBS-EP (10 mM HEPES, 150 mM NaCl, 3.4 mM EDTA, 0.005% Polysorbate 20 (v/v)). A BIAcore CM5 sensor chip was subjected to a pre-conditioning procedure. Sequentially 0.1% SDS, 50 mM NaOH, 10 mM HCl and 100 mM $H_3PO_4$ was injected for 30 sec over the flow cells FC1, FC2, FC3 and FC4. The amine coupling procedure was done according to the manufacturers instructions using the BIAcore 3000 wizard v. 4.1.

In order to perform crossblocking experiments with chimeric or humanized antibodies, after an EDC/NHS activation of the sensor surface a polyclonal goat anti-human IgG antibody (Jackson) was immobilized on all sensor flow cells (FCs). 30 µg/ml polyclonal goat anti-human IgG antibody in 10 mM NaAc pH 5.0 was used at 10 µl/min for 7 min to immobilize 10.000 RU of the antibody capturing system. The surface was deactivated by saturation with ethanolamine. The human capture system sensor was conditioned with 5 cycles of binding of huIgG analyte (Bayer) at 10 µl/min for 2 min and regeneration with 10 mM Glycine pH 1.7 at 30 µl/min for 3 min.

At a flow rate of 10 µl/min the primary mAb was injected for 3 min into FC1-FC4. Free binding capacity of the sensor's capturing system was blocked using a 3 min injection into FC1-FC4 at 10 µl/min of a cocktail from 50 µg/ml huIgG (Bayer) in HBS-EP buffer. Subsequently, the antigen rhuIL17-A was injected at 10 µl/min for 3 min into FC1-FC4 to saturate the primary antibodies binding capacity. A second injection into FC1-FC4 at 30 µl/min for 3 min was performed before the secondary antibodies were separately injected at 30 µl/min for 3 min into the flow cells FC1, FC2, FC3 and FC4. The sensor was regenerated using 10 mM Glycine pH 1.75 at 30 µl/min for 3 min.

First, the 0 nM analyte injection was subtracted from all sensorgrams in order to correct the dissociation of the primary antibodies from the polyclonal goat anti-human IgG capturing system. A quotient was formed by the response signal of the secondary antibody and the primary antibody. The quotient carries the name Molar Ratio (MR) and indicates the accessibility of the epitope region.

The Molar Ratio values were listed in a matrix. Homologous mAb combinations served as a control, whether the blocking procedures had been successfully performed. The cut off was defined by homologous mAb combinations.

The cut off in the crossblocking experiments was set to the Mab106 homogenous assay format (9%). Molar Ratio values above MR=15% relate to access to independent epitopes.

The results from the Epitope Mapping (see Table 2) indicate that the Mab K106 and its derivative Mab107 bind to a different epitope region than NVP-AIN-497. Moreover, Mab K106 covers a different epitope than eBio64CAP17, and the same epitope region than Mab317.

TABLE 2

Epitope Mapping results

| Antibody 1 | Antibody 2 | Molar Ratio[%] |
|---|---|---|
| eBio64CAP17 | 106 | 41 |
| NVP-AIN-497 | 106 | 17 |
| Mab317 | 106 | 11 |
| NVP-AIN-497 | 107 | 21 |
| Mab317 | Mab317 | 0 |
| 106 | 106 | 9 |
| eBio64CAP17 | eBio64CAP17 | 7 |
| NVP-AIN-497 | NVP-AIN-497 | 6 |

The cut off of the analysis is defined by the homogenous assay combinations. (106, 9%); (AIN-457, 6%); (eBio64CAP17, 7%); (Mab317, 0%). Here the cut off was set to the homogenous Mab106 assay.

Example 6

Cytokine Release Assay, Inhibition of IL-17A Induced hIL-8 Release

The assay is performed to detect hIL-8 production of CCD-25SK cells after stimulation with IL-17A and TNF-alpha with preincubation of anti-IL-17 antibodies. CCD-25SK cells express the IL-17 receptor, and soluble IL-17A binds to the receptors. Antibodies against IL-17A bind to IL-17A. The mechanism only works in the presence of TNFα. Through the binding of IL-17A to the IL-17 receptor, the cells produce hIL-8, which is detected by ELISA as a read out. The measured hIL-8 give the information in which concentrations anti-IL-17 antibodies inhibit the stimulation of CCD-25SK cells by IL-17.

CCD-25SK cells were seeded with a cell density of $2.5 \times 10^4$ cells/well in a 48-well plate (volume 0.45 ml/well) and incubated for 24 h at 37° C. and 5% $CO_2$. After overnight incubation, the cells were treated with anti-IL-17 antibodies for 30 min, with end concentrations of 9000; 3000; 1000; 333.3; 111.1; 37.03; 12.34; and 4.11 ng/ml. Each antibody dilution series was made with medium, 50 µl/well (10× concentrated). After 30 min, the cells were stimulated with a mixture of 10 ng/ml IL-17A and 50 pg/ml TNF-alpha, 50 µl/well (10× concentrated) and incubated for 24 h at 37° C. and 5% $CO_2$. After overnight incubation the supernatants were transferred to 96-well plates and frozen at −20° C. as intermediates for hIL-8 ELISA.

hIL-8 ELISA was performed as follows: Diluted capture antibody (100 µl) was added to each well and incubated overnight at 4° C. Dilutions were made with coating buffer. Plates were aspirated, washed with 200 µl/well 3×, blocked with 200 µl/well assay diluent, and incubated for 1 h at RT. The plates were aspirated and washed with 200 µl/well 3×. 100 µl standard and samples were added and incubated for 2 h at RT. Standard dilution series: 400 pg/ml; 200 pg/ml; 100 pg/ml; 50 pg/ml; 25 pg/ml; 12.5 pg/ml; 6.3 pg/ml and assay diluent as negative control. Sample dilution was 1:200. Plates were aspirated and washed with 250 µl/well 4×, and 100 µl conjugate was added to each well. The conjugate was prepared with detection antibody and enzyme reagent 1:250 diluted in assay diluent. Plates were aspirated and washed with 250 µl/well 6×. 100 µl substrate was added to each well and incubated for 12 min. After incubation the reaction was stopped with 50 µl/well 1M $H_2SO_4$. Read out was performed at 450 nm within 30 min with λ correction at 570 nm. Results are shown in Table 3 ($IC_{50}$ values measured in relation to a maximal inhibition of 80%).

TABLE 3

| Antibody | IL-6 Neutralization IC50 (nM) | IL-8 Neutralization IC50 (nM) |
|---|---|---|
| 3C1 | 1.0 | 1.0 |
| 106 | 1.0 | 1.0 |
| Mab 317 | 5.5 | 5.5 |

Example 7

Synoviocyte Cytokine Release Assay, Inhibition of IL-17A Induced hIL-6 and hIL-8

Primary human fibroblast like synoviocytes (HFLS) cells produce hIL-6 and hIL-8 in response to IL-17A stimulation. The assay is performed to measure the inhibition of this IL-17A stimulated hIL-6 and hIL-8 production by HFLS cells following preincubation of the cells with anti-IL-17 antibodies prior to stimulation.

HFLS cells were seeded with a cell density of $4 \times 10^5$ cells/ ml in a volume of 0.5 ml in a 48-well plate, and incubated overnight at 37° C. and 5% $CO_2$ to adhere. After overnight incubation, the media was replaced with 400 µl fresh media and the cells were treated with anti-IL-17 antibodies for 30 min across a range of antibody concentrations (10000, 3000, 1000, 300, 100, 30, 10, 3, 0 ng/ml). Each antibody dilution series was made with medium using 50 μl/well (10× concentrated). After 30 min the cells were stimulated with 100 ng/ml IL-17A (50 μl of 1000 ng/ml 10× concentration) and incubated overnight (18 h) at 37° C. and 5% $CO_2$. After the incubation period, supernatants were transferred into fresh tubes and either analyzed immediately or stored at −80° C. until analysis by ELISA. For the hIL-6 and hIL-8 ELISAs, 100 μl diluted capture antibody was added to each well and incubated overnight at 4° C. Dilutions were made with coating buffer. Plates were aspirated, washed with 200 μl/well 3×, blocked with 200 μl/well assay diluent, and incubated for 1 h at RT. The plates were aspirated and washed with 200 μl/well 3×. 100 μl standard and samples were added and incubated for 2 h at RT according to the manufacturer's instructions. Plates were aspirated and washed with 250 μl/well at least 3×. 100 μl conjugate was added to each well. The conjugate was prepared with detection antibody and enzyme reagent 1:250 diluted in assay diluent. Plates were aspirated and washed with 250 μl/well at least 3×. 100 μl substrate was added to each well and incubated until sufficient colour had developed for reading. After incubation the reaction was stopped with 50 μl/well 1M $H_2SO_4$ and read on the plate reader at a wavelength of 450 nm within 30 min. The results are shown in Table 4.

TABLE 4

| Antibody | IL-6 Neutralization $IC_{50}$ (nM) (using 100 ng/ml IL-17A) | IL-8 Neutralization $IC_{50}$ (nM) (using 100 ng/ml IL-17A) |
|---|---|---|
| 3C1 | 1.9 | 1.4 |
| 106 | 2.1 | 1.6 |
| NVP-AIN-457 | 5.0 | 4.2 |

Example 8

Crossreactivity with Cynomolgus IL-17A (Binding Assay)

The binding assay was performed according to example 2. Results are shown in Table 5.

TABLE 5

| Antibody | Relative binding to human IL-17A | Relative binding to cynomolgus IL-17A |
|---|---|---|
| 3C1 | 1 | n.d. |
| 106 | 1 | 0.87 |
| 106 (IgG4) | 1 | 0.87 |
| 106 (IgG1-LALA) | 1 | 1.0 |
| NVP-AIN-497 | 1 | 0.6 |

Example 9

Cynomolgus Monkey (*Maccaca Fasicularis*) Cytokine Release Assay, Inhibition of Cynomolgus IL-17A Induced IL-6 and IL-8 Production Cynomolgus dermal fibrobasts (CDF) cells produce cynomolgus IL-6 and IL-8 in response to human or cynomolgus IL-17A stimulation. The assay is performed to measure the inhibition of this cynomolgus IL-17A stimulated IL-6 and IL-8 production by CDF cells following preincubation of the cells with anti-IL-17 antibodies raised against human IL-17 prior to stimulation.

CDF cells were seeded with a cell density of $2\times10^5$ cells/ml in a volume of 0.5 ml in a 48-well plate, and incubated overnight at 37° C. and 5% $CO_2$ to adhere. After overnight incubation, the media was replaced with 400 μl fresh media and the cells were treated with anti-IL-17 antibodies for 30 min across a range of antibody concentrations (10000, 3000, 1000, 300, 100, 30, 10, 3, 0 ng/ml). Each antibody dilution series was made with medium using 50 μl/well (10× concentrated). After 30 min the cells were stimulated with 100 ng/ml IL-17A (50 μl of 1000 ng/ml 10× concentration) and incubated overnight (18 h) at 37° C. and 5% $CO_2$. After the incubation period, supernatants were transferred into fresh tubes and either analyzed immediately or stored at −80° C. until analysis by ELISA. hIL-6 and hIL-8 ELISA were shown to be cross-reactive with their respective cynomolgus cytokines and were used to quantitiate cytokine levels. For the ELISAs, 100 μl diluted capture antibody was added to each well and incubated overnight at 4° C. Dilutions were made with coating buffer. Plates were aspirated, washed with 200 μl/well 3×, blocked with 200 μl/well assay diluent, and incubated for 1 h at RT. The plates were aspirated and washed with 200 μl/well 3×. 100 standard and samples were added and incubated for 2 h at RT according to the manufacturer's instructions. Plates were aspirated and washed with 250 μl/well at least 3×. 100 μl conjugate was added to each well. The conjugate was prepared with detection antibody and enzyme reagent 1:250 diluted in assay diluent. Plates were aspirated and washed with 250 μl/well at least 3×. 100 μl substrate was added to each well and incubated until sufficient colour had developed for reading. After incubation the reaction was stopped with 50 μl/well 1M $H_2SO_4$ and read on the plate reader at a wavelength of 450 nm within 30 min. The results are shown in Table 6.

TABLE 6

| Antibody | IL-6 Neutralization IC50 (nM) (using 100 ng/ml IL-17A) | IL-8 Neutralization IC50 (nM) (using 100 ng/ml IL-17A) |
|---|---|---|
| 3C1 | 1.3 | 1.1 |
| 106 | 0.7 | 0.6 |
| NVP-AIN-457 | >10 | >10 |

Example 10

Europium-Based ADCC Assay

PBL are isolated by Ficoll Paque Plus Gradient Centrifugation: A heparinized blood sample was diluted 1:1 with PBS. 8 ml of the diluted blood was overlayed onto Ficoll and centrifuged for 30 min at 800×g. The cells (PBLs) were collected, washed with RPMI1640/10% FCS and resuspended in cell culture medium. The cells were diluted to $2.5\times10^6$ cells/ml. (this will result in a effector/target ratio of 25:1, as $5\times10^3$ target cells are used per well).

Target cells are labelled with BADTA (2,2':6',2"-terpyridine-6,6"-dicarboxylic acid acetoxymethylester): Cells were harvested by adding Accutase™ (Millipore), washed once and diluted to $1\times10^6$ cells/ml. 2.5 μl BADTA/$1\times10^6$ cells were added and incubated for 35 min at 37° C./5% $CO_2$. After labelling period the cells were diluted with 10 ml culture medium, centrifuged at 200×g for 10 min and supernatant aspirated. This step was repeated 3× with culture medium/2 mM Probenicid and the sample was diluted to $1\times10^5$ cells/ml, centrifuged at 300×g for 5 min, supernant taken off and 50 μl pipetted into the wells intended for the background controls.

Background: the 50 μl aliquot, diluted with 100 μl medium. Spontaneous lysis: 50 μl of the labelled target cell suspension; add 100 μl culture medium and incubate 2 h/37° C. as the rest of the samples. Maximal lysis: 50 μl/well of the labelled target cell suspension; add 100 μl Triton® X-100 (0.5% in PBS) and incubate 2 h/37° C. Lysis control without antibodies: 50 μl/well of the labelled target cell suspension; add 50 μl culture medium; add 50 μl of effector cells, 2 h at 37° C. Lysis control without effector cells: 50 μl/well of the labelled target cell suspension; add 50 μl culture medium add 50 ml antibody solution in highest concentration used and incubate 2 h/37° C.

At the end of the incubation period the 96 well plate was centrifuged at 100 rpm. 20 μl of each supernatant was transferred into a OptiPlate™ HTRF-96 (Packard) and 200 ml Europium solution was added and incubated for 15 min on a shaker. Fluorescence was measured as for time resolved fluorescence and spontaneous release and specific release were calculated according to the following formula:

$$\text{Specific release in \%} = \frac{\text{specific lysis (counts)} - \text{spontaneous lysis (counts)} \times 100}{\text{maximal lysis (counts)} - \text{spontaneous lysis (counts)}}$$

No significant specific release (ADCC) was measured after addition of antibody 106.

Example 11

CDC Assay

Cells were harvested by adding trypsin, washed, diluted to $1 \times 10^5$ cells/ml and 100 μl/well added to a 96-well flat bottom microtiter plate. Antibody was added (antibody-ligand complex respectively) at a 6-fold endconcentration in a volume of 25 μl in medium. After 30 min incubation time 25 μl freshly dissolved baby rabbit complement (Cedarlane CL3441, 1 ml lyophilized, dilute freshly in 4 ml double distilled water) was added to a complement end concentration of 1:24. After a 20 h incubation period 50 μl supernatant was taken off and 100 μl Cell Titer Glo® reagent (Promega Corp.) was added to the remaining 100 μl supernatant. The plate was shaked for 2 min on an orbital shaker, 100 μl/well was transferred into a black luminescence microtiter plate (Costar) and luminescence was measured.

Controls: Medium control (target cells+50 μl medium); maximal lysis (target cells+50 μl 0.5% Triton X-100), complement control (target cells+25 μl medium+25 μl complement).

Results: no complement depending cytotoxicity (CDC) could be detected with the anti-IL17 antibody 106.

The invention claimed is:

1. An antibody binding to human IL-17, comprising a heavy chain and a light chain, characterized in that:

the heavy chain comprises a variable domain comprising a CDR3 region of SEQ ID NO:1, a CDR2 region selected from SEQ ID NO:2 and SEQ ID NO:9, and a CDR1 region of SEQ ID NO:3; and the light chain variable domain comprises a CDR3 region of SEQ ID NO:4, a CDR2 region of SEQ ID NO:5, and a CDR1 region of SEQ ID NO:6.

2. The antibody of claim 1, wherein the heavy chain variable domain comprises SEQ ID NO:7 or SEQ ID NO:10.

3. The antibody of claim 2, wherein the light chain variable domain comprises SEQ ID NO:8.

4. The antibody of claim 1, characterized in being a chimeric or humanized antibody of antibody 3C1 (DSM ACC2941).

5. The antibody of claim 1, having the human IgG1 isotype modified:
  in the hinge region at amino acid position 216-240;
  in the second inter-domain region at amino acid position 327-331 between $C_H2$ and $C_H3$; or
  in both the hinge region and the second inter-domain region.

6. A pharmaceutical composition comprising the antibody according to claim 1, and a pharmaceutically acceptable excipient.

7. The pharmaceutical composition of claim 6, wherein said antibody binds to the same IL-17 epitope to which monoclonal antibody 3C1 (DSM ACC2941) binds.

8. An antibody binding to human IL-17, characterized by binding to the same IL-17 epitope to which monoclonal antibody 3C1 (DSM ACC2941) binds, being of human IgG1 isotype modified in the hinge region at amino acid position 216-240, and/or in the second inter-domain region at amino acid position 327-331 between $C_H2$ and $C_H3$.

9. The antibody according to claim 8, characterized by comprising mutations L234A (alanine instead of leucine at amino acid position 234) and L235A.

10. An antibody binding to human IL-17, wherein the antibody is produced by the hybridoma cell line DSM ACC2941.

11. A hybridoma cell line DSM ACC2941.

12. A method for treating multiple sclerosis, rheumatoid arthritis, psoriasis, Crohn's disease, chronic obstructive pulmonary disease (COPD), asthma, or transplant rejection, comprising administering an effective amount of the antibody of claim 1 to a subject diagnosed with multiple sclerosis, rheumatoid arthritis, psoriasis, Crohn's disease, chronic obstructive pulmonary disease (COPD), or asthma, or at risk of transplant rejection.

13. The method of claim 12, wherein said antibody binds to the same IL-17 epitope to which monoclonal antibody 3C1 (DSM ACC2941).

14. The method of claim 13, wherein said antibody comprises antibody 3C1 (DSM ACC2941).

15. An isolated nucleic acid encoding an antibody binding to IL-17, characterized in that said antibody comprises a heavy chain CDR3 region of SEQ ID NO: 1, a heavy chain CDR2 region of SEQ ID NO:2 or SEQ ID NO:9, a heavy chain CDR1 region of SEQ ID NO:3, a light chain CDR3 region of SEQ ID NO: 4, a light chain CDR2 region of SEQ ID NO:5 and a light chain CDR1 region of SEQ ID NO:6.

16. An expression vector comprising the nucleic acid of claim 15.

17. A method for producing an antibody encoded by the nucleic acid of claim 15, comprising: culturing a host cell transformed with an expression vector comprising said nucleic acid under conditions suitable for the expression of said antibody; and recovering said antibody from the host cell culture.

* * * * *

SEQUENCE LISTING

```
<160> NUMBER OF SEQ ID NOS: 12

<210> SEQ ID NO 1
<211> LENGTH: 13
<212> TYPE: PRT
<213> ORGANISM: Mus musculus

<400> SEQUENCE: 1

Asp Gly Asp Tyr Gly Ser Ser Tyr Gly Ala Met Asp Tyr
1               5                   10

<210> SEQ ID NO 2
<211> LENGTH: 16
<212> TYPE: PRT
<213> ORGANISM: Mus musculus

<400> SEQUENCE: 2

Val Ala Ile Ile Lys Ser Gly Gly Ser Tyr Ser Tyr Tyr Pro Asp Ser
1               5                   10                  15

<210> SEQ ID NO 3
<211> LENGTH: 10
<212> TYPE: PRT
<213> ORGANISM: Mus musculus

<400> SEQUENCE: 3

Gly Phe Thr Phe Ser Asp Tyr Thr Met Leu
1               5                   10

<210> SEQ ID NO 4
<211> LENGTH: 9
<212> TYPE: PRT
<213> ORGANISM: Mus musculus

<400> SEQUENCE: 4

Leu Gln Tyr Asp Ala Phe Pro Pro Tyr
```

-continued

<210> SEQ ID NO 5
<211> LENGTH: 7
<212> TYPE: PRT
<213> ORGANISM: Mus musculus

<400> SEQUENCE: 5

Arg Ala Asn Arg Leu Val Asp
1               5

<210> SEQ ID NO 6
<211> LENGTH: 11
<212> TYPE: PRT
<213> ORGANISM: Mus musculus

<400> SEQUENCE: 6

Arg Ala Ser Gln Asp Ile Asn Ser Tyr Leu Ser
1               5                   10

<210> SEQ ID NO 7
<211> LENGTH: 122
<212> TYPE: PRT
<213> ORGANISM: Mus musculus

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Thr Met Leu Trp Val Arg Gln Ala Pro Gly Lys Gly Leu Glu Trp Val
        35                  40                  45

Ala Ile Ile Lys Ser Gly Gly Ser Tyr Ser Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Asp Tyr Gly Ser Ser Tyr Gly Ala Met Asp Tyr Trp
            100                 105                 110

Gly Gln Gly Thr Leu Val Thr Val Ser Ser
        115                 120

<210> SEQ ID NO 8
<211> LENGTH: 108
<212> TYPE: PRT
<213> ORGANISM: Mus musculus

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Gln Pro
65                  70                  75                  80

Glu Asp Phe Ala Thr Tyr Tyr Cys Leu Gln Tyr Asp Ala Phe Pro Pro

```
                    85                  90                  95
Tyr Thr Phe Gly Gln Gly Thr Lys Leu Glu Ile Lys
                100                 105

<210> SEQ ID NO 9
<211> LENGTH: 19
<212> TYPE: PRT
<213> ORGANISM: Mus musculus

<400> SEQUENCE: 9

Val Ser Ile Ile Lys Ser Gly Gly Ser Tyr Ser Tyr Tyr Pro Asp Ser
1               5                   10                  15

Val Lys Gly

<210> SEQ ID NO 10
<211> LENGTH: 122
<212> TYPE: PRT
<213> ORGANISM: Mus musculus

<400> SEQUENCE: 10

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Leu Trp Ile Arg Gln Ala Pro Gly Lys Gly Leu Glu Trp Val
        35                  40                  45

Ser Ile Ile Lys Ser Gly Gly Ser Tyr Ser Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Asp Tyr Gly Ser Tyr Gly Ala Met Asp Tyr Trp
            100                 105                 110

Gly Gln Gly Thr Leu Val Thr Val Ser Ser
        115                 120

<210> SEQ ID NO 11
<211> LENGTH: 330
<212> TYPE: PRT
<213> ORGANISM: Mus musculus

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
```

```
              115                 120                 125
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 107
<212> TYPE: PRT
<213> ORGANISM: Mus musculus

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```